US00PP34877P2

(12) United States Plant Patent
Ullrich

(10) Patent No.: US PP34,877 P2
(45) Date of Patent: Jan. 3, 2023

(54) ROSE PLANT NAMED 'ESM P023'

(50) Latin Name: *Rosa hybrida*
Varietal Denomination: 'ESM P023'

(71) Applicant: TECNOVIV LLC, Miami, FL (US)

(72) Inventor: Clarisse Ullrich, Quito (EC)

(73) Assignee: TECNOVIV LLC, Miami, FL (US)

( * ) Notice: Subject to any disclaimer, the term of this patent is extended or adjusted under 35 U.S.C. 154(b) by 22 days.

(21) Appl. No.: 17/669,066

(22) Filed: Feb. 10, 2022

(51) Int. Cl.
*A01H 5/02* (2018.01)
*A01H 6/74* (2018.01)

(52) U.S. Cl.
USPC ..... Plt./103
CPC ..... *A01H 6/749* (2018.05)

(58) Field of Classification Search
USPC ..... Plt./103
CPC ..... A01H 6/749
See application file for complete search history.

*Primary Examiner* — Anne Marie Grunberg
(74) *Attorney, Agent, or Firm* — C. Anne Whealy

(57) ABSTRACT

A new and distinct cultivar of Rose plant named 'ESM P023', characterized by its strong and vigorous root system; upright and strong thick stems; vigorous growth habit; dark green-colored leaves; and numerous white-colored flowers arranged in terminal sprays.

1 Drawing Sheet

Botanical designation: *Rosa hybrida.*
Cultivar denomination: 'ESM P023'.

STATEMENT REGARDING PRIOR DISCLOSURES BY INVENTOR AND APPLICANT/ASSIGNEE

An European Community Plant Breeder's Rights application for the instant plant was filed by the Applicant/Assignee of the instant application, Tecnoviv LLC of Miami, Fla. on Jun. 27, 2019, application number 2019/1593. Foreign priority is not claimed to this European Community Plant Breeder's Rights application.

A Kenyan Plant Breeder's Rights application for the instant plant was filed by the Applicant/Assignee of the instant application, Tecnoviv LLC of Miami, Fla. on Aug. 9, 2019, application number ROS 19 1744. Foreign priority is not claimed to this Kenyan Plant Breeder's Rights application.

An Ecuadorian Plant Breeder's Rights application for the instant plant was filed by the Applicant/Assignee of the instant application, Tecnoviv LLC of Miami, Fla. on Aug. 27, 2019, application number 1607-19. Foreign priority is not claimed to this Ecuadorian Plant Breeder's Rights application.

A Columbian Plant Breeder's Rights application for the instant plant was filed by the Applicant/Assignee of the instant application, Tecnoviv LLC of Miami, Fla. on Jun. 26, 2020, application number A202687. Foreign priority is not claimed to this Ecuadorian Plant Breeder's Rights application.

The Inventor and Applicant/Assignee assert that no publications nor advertisements relating to sales, offers for sale or public distribution occurred more than one year prior to the effective filing date of this application. Any information about the claimed plant would have been obtained from a direct or indirect disclosure from the Inventor and/or Applicant/Assignee. Inventor and Applicant/Assignee claim a prior art exception under 35 U.S.C. 102(b)(1) for disclosure and/or sales prior to the filing date but less than one year prior to the effective filing date.

BACKGROUND OF THE INVENTION

The present Invention relates to a new and distinct cultivar of Rose plant, botanically known as *Rosa hybrida*, commercially used as rootstock plant, and hereinafter referred to by the name 'ESM P023'.

The new Rose plant is a product of a planned breeding program conducted by the Inventor in El Quinche, Pichincha, Ecuador. The objective of the breeding program was to develop new and improved rootstock varieties with vigorous growth habit, thick stems and strong root systems.

The new Rose plant originated from a cross-pollination made by the Inventor in February, 2015 of a proprietary Rose selection identified as Line R881, not patented, as the female, or seed, parent with a proprietary Rose selection identified as Line R744, not patented, as the male, or pollen, parent. The new Rose plant was discovered and selected by the Inventor as a single flowering plant within the progeny of the stated cross-pollination in a controlled greenhouse environment in El Quinche, Pichincha, Ecuador in January, 2016.

Asexual reproduction of the new Rose plant by bud grafting in El Quinche, Pichincha, Ecuador since May, 2016 has shown that the unique features of this new Rose plant are stable and reproduced true to type in successive generations of asexual reproduction.

SUMMARY OF THE INVENTION

Plants of the new Rose have not been observed under all possible combinations of environmental conditions and cultural practices. The phenotype may vary somewhat with variations in environmental conditions such as temperature and light intensity, without however, any variance in genotype.

The following traits have been repeatedly observed and are determined to be the unique characteristics of 'ESM P023'. These characteristics in combination distinguish 'ESM P023' as a new and distinct Rose plant:

1. Strong and vigorous root system.
2. Upright and strong thick stems.
3. Vigorous growth habit.
4. Dark green-colored leaves.
5. Numerous white-colored flowers arranged in terminal sprays.

Plants of the new Rose differ from plants of the female parent selection in the following characteristics:

1. Plants of the new Rose are more vigorous and have longer stems than plants of the female parent selection.
2. Plants of the new Rose are more freely flowering than plants of the female parent selection.
3. Plants of the new Rose have smaller flowers than plants of the female parent selection.

Plants of the new Rose differ from plants of the male parent selection in the following characteristics:

1. Plants of the new Rose are more vigorous and have longer stems than plants of the male parent selection.
2. Flowering stems of plants of the new Rose have longer postproduction longevity than flowering stems of plants of the male parent selection.

Plants of the new Rose can also be compared to plants of *Rosa hybrida* 'Bright Beauty' (also known as ROS 4504), not patented. In side-by-side comparisons, plants of the new Rose differ from plants of 'Bright Beauty' in the following characteristics:

1. Developed stems of plants of the new Rose have more anthocyanin than developed stems of plants of 'Bright Beauty'.
2. Leaves of plants of the new Rose are glossier than leaves of plants of 'Bright Beauty'.

BRIEF DESCRIPTION OF THE PHOTOGRAPH

The accompanying colored photographic sheet illustrates the overall appearance of the new Rose plant showing the colors as true as it is reasonably possible to obtain in colored reproductions of this type. Colors in the photograph may differ slightly from the color values cited in the detailed botanical description which accurately describe the colors of the new Rose plant.

On the left of the photographic sheet is a side perspective view of a typical flowering stem of 'ESM P023'.

At the upper right of the photographic sheet is a close-up view of typical developing and developed flowers of 'ESM P023'.

At the lower right of the photographic sheet is a close-up view of a typical inflorescence of 'ESM P023'.

And at the center of the photographic sheet are close-up views of the upper and lower surfaces of typical leaves of 'ESM P023'.

DETAILED BOTANICAL DESCRIPTION

The aforementioned photographs, following observations and measurements describe plants grown in ground beds in a polyethylene-covered greenhouse in Quito, Ecuador and under typical Rose production practices. Plants were four years and 40 weeks old when the photographs and the description were taken. During the production of the plants, day temperatures ranged from 16° C. to 30 ° C., night temperatures ranged from 12° C. to 16° C. and light levels ranged from 800 to 1,200 foot-candles. In the following description, color references are made to The Royal Horticultural Society Colour Chart, 2015 Edition, except where general terms of ordinary dictionary significance are used.

Botanical classification: *Rosa hybrida* 'ESM P023'.

Parentage:

*Female, or seed, parent.*—Proprietary seedling selection of *Rosa hybrida* identified Line R881, not patented.

*Male, or pollen, parent.*—Proprietary seedling selection of *Rosa hybrida* identified Line R744, not patented.

Propagation:

*Type.*—By bud grafting.

*Time to initiate roots, summer.*—About 15 days at temperatures about 26° C. to 30° C.

*Time to produce a rooted young plant, summer.*—About 30 days at temperatures about 22° C. to 26° C.

*Root description.*—Strong and vigorous root system; roots, medium in thickness and fibrous; typically greyish brown in color, actual color of the roots is dependent on substrate composition, water quality, fertilizers, substrate temperature and age of roots.

*Rooting habit.*—Moderately freely branching; dense.

Plant description:

*Plant and growth habit.*—Perennial shrub; upright and strong flowering stems; typically grown as a spray-type; vigorous growth habit and rapid growth rate; freely branching habit with typically about five to ten primary branches each with about two to four secondary branches.

*Plant height.*—About 208.5 cm.

*Plant width (spread).*—About 176.8 cm.

*Lateral branches.*—Length: About 160 cm. Diameter: About 9.1 mm. Internode length: About 3.5 cm. Texture and luster: Smooth, glabrous; matte. Strength: Moderately strong. Color, developing: Close to 144A to 144B. Color, developed: Close to 144A and 182A. Thorns: Density: About one thorn per linear cm. Height: About 3.6 mm. Length, at base: About 1 mm. Color, immature: Close to 174A and 146D. Color, mature: Close to 183A.

Leaf description:

*Arrangement.*—Alternate; compound with typically seven to nine leaflets per leaf.

*Leaf length.*—About 17.8 cm.

*Leaf width.*—About 7.7 cm.

*Leaflet length.*—About 14.1 cm.

*Leaflet width.*—About 3.4 cm.

*Leaflet shape.*—Oval.

*Leaflet apex.*—Acuminate.

*Leaflet base.*—Obtuse.

*Leaflet margin.*—Serrate.

*Leaflet texture and luster, upper surface.*—Smooth, glabrous; slightly glossy.

*Leaflet texture and luster, lower surface.*—Smooth, glabrous; matte.

*Leaflet venation pattern.*—Pinnate.

*Leaflet color.*—Developing leaflets, upper surface: Close to 137A. Developing leaflets, lower surface: Close to 138A. Fully expanded leaflets, upper surface: Close to 139A; venation, close to 146C. Fully expanded leaflets, lower surface: Close to 147B; venation, close to 146C.

*Petioles*.—Length: About 1.1 cm. Diameter: About 3 mm. Strength: Weak. Texture and luster, upper and lower surfaces: Glandular, glabrous; matte. Color, upper and lower surfaces: Close to 144A; glands, close to 182A.

*Stipules*.—Arrangement and appearance: Two, adnate to the petiole, leafy in appearance. Length: About 1.3 cm. Width: About 6 mm. Shape: Roughly deltoid. Apex: Acuminate, tapered. Base: Tapered. Margin: Variable. Texture and luster, upper and lower surfaces: Glandular, margins, pubescent; matte. Venation pattern: Pinnate.

Flower description:

*Flower type and arrangement*.—Symmetrical rosette flowers; flowers arranged in terminal inflorescences with about 20 to 63 flowers developing per inflorescence; flowers face upright.

*Flowering season*.—Plants of the new Rose flower year-round under greenhouse conditions; early flowering habit, plants begin flowering about 10 to 17 days after pruning.

*Flower diameter*.—About 3.7 cm.

*Flower depth* (*height*).—About 1 cm.

*Flower longevity*.—Flowers maintain good substance for about 13 to 20 days on the plant; flowers persistent.

*Fragrance*.—Strongly fragrant; pleasant.

*Flower buds*.—Length: About 1.2 cm. Diameter: About 8 mm. Shape: Ovoid. Texture and luster: Smooth to rough, glabrous; matte. Color: Close to 36C to 36D.

*Petals*.—Quantity: About five per flower arranged in a single whorl. Length: About 1.5 cm. Width: About 1.5 cm. Shape: Nearly orbicular. Apex: Emarginate. Base: Tapering. Margin: Entire; not undulate. Texture and luster, upper and lower surfaces: Smooth, glabrous; matte. Color: When opening, upper and lower surfaces: Close to NN155D. Fully opened, upper and lower surfaces: Close to NN155D; venation, close to NN155D; color becoming closer to 158A, 161B and 164B with subsequent development.

*Sepals*.—Quantity per flower: Typically five in a single whorl. Length: About 1.1 cm. Width: About 3.7 mm. Shape: Ovate. Apex: Tapered. Base: Rounded. Margin: Entire. Texture and luster, upper surface: Pubescent; matte. Texture and luster, lower surface: Smooth, glabrous; matte. Color: When opening, upper surface: Close to 143C to 143D. When opening, lower surface: Close to 144B to 144C. Fully opened, upper surface: Close to 144B to 144C. Fully opened, lower surface: Close to 144B to 144D.

*Peduncles*.—Length: About 2.3 cm. Diameter: About 1 mm. Strength: Moderately strong to weak. Texture and luster: Pubescent; matte. Color: Close to 143B to 143C.

*Reproductive organs*.—Stamens: Quantity: About 109 per flower. Filament length: About 7.5 mm. Filament color: Close to 162B. Anther size: About 1.5 mm by 1.3 mm. Anther shape: Reniform, bilobed. Anther color: Close to 162A and 163B. Pollen amount: Moderate to abundant. Pollen color: Close to N163D. Pistils: Quantity: One per flower. Pistil length: About 1.1 cm. Stigma diameter: About 2 mm. Stigma shape: Conical. Stigma color: Close to 144B and 151B. Style length: About 3 mm. Style color: Close to 142B. Ovary color: Close to 155C. Receptacle height: About 5.6 mm. Receptacle diameter: About 3 mm. Receptacle shape: Oval. Receptacle texture: Smooth, glabrous. Receptacle color: Close to 143B to 143C. Fruits and seeds: To date, fruit and seed development have not been observed on plants of the new Rose.

Pathogen & pest tolerance: To date, plants of the new Rose have not been observed to be tolerant to pathogens and pests common to Rose plants.

Garden performance: Plants of the new Rose have been observed to tolerate wind, rain and temperatures ranging from 9° C. to 23° C.

It is claimed:

1. A new and distinct Rose plant named 'ESM P023' as illustrated and described.

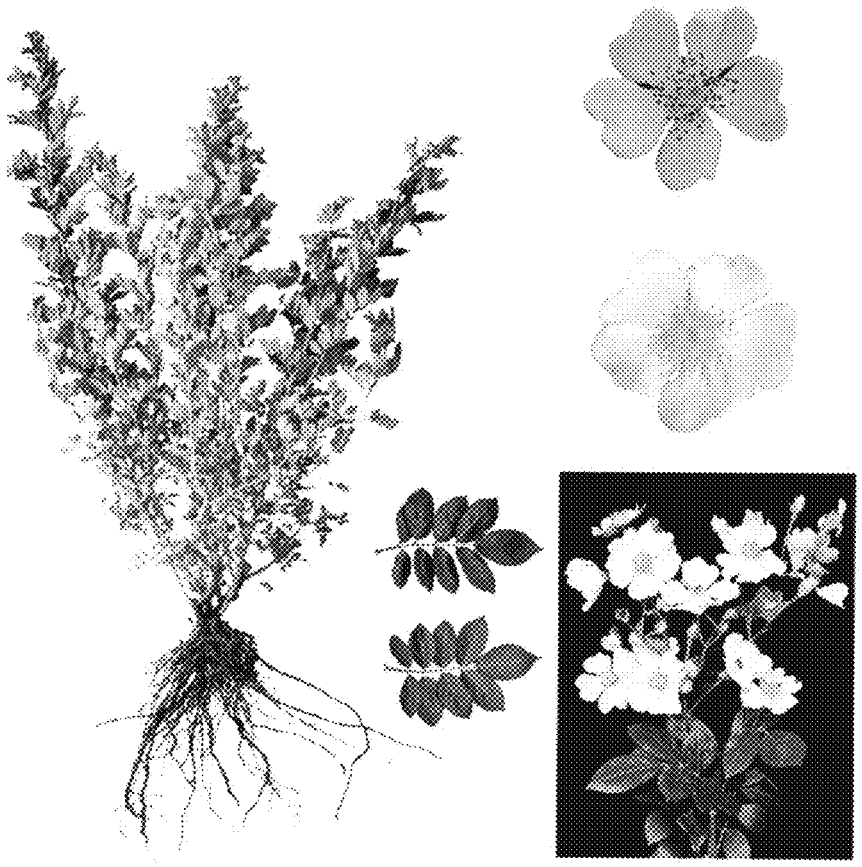

* * * * *